(12) United States Patent
Hasegawa et al.

(10) Patent No.: US 8,328,774 B2
(45) Date of Patent: Dec. 11, 2012

(54) VISION CORRECTIVE JIG AND COOLING FLUID INJECTION TOOL FOR THE JIG

(76) Inventors: Tokuichiro Hasegawa, Yokohama (JP); Sakichi Hasegawa, Yokohama (JP)

( * ) Notice: Subject to any disclaimer, the term of this patent is extended or adjusted under 35 U.S.C. 154(b) by 202 days.

(21) Appl. No.: 12/808,893

(22) PCT Filed: May 26, 2008

(86) PCT No.: PCT/JP2008/059668
§ 371 (c)(1),
(2), (4) Date: Jun. 17, 2010

(87) PCT Pub. No.: WO2009/090763
PCT Pub. Date: Jul. 23, 2009

(65) Prior Publication Data
US 2011/0166535 A1  Jul. 7, 2011

(30) Foreign Application Priority Data
Jan. 16, 2008  (JP) ................. 2008-006430

(51) Int. Cl.
*A61M 35/00* (2006.01)
*A61B 18/18* (2006.01)
*G02C 7/04* (2006.01)
*B23B 1/00* (2006.01)

(52) U.S. Cl. ......... 604/294; 424/428; 424/429; 606/27; 606/28; 606/48; 606/49; 606/50; 606/166; 604/289; 623/5.13

(58) Field of Classification Search .................. 424/428, 424/429; 606/27–28, 48–50, 166; 604/289; 623/5.13
See application file for complete search history.

(56) References Cited

U.S. PATENT DOCUMENTS

| | | | | |
|---|---|---|---|---|
| 3,760,807 A | * | 9/1973 | Neefe | ............................ 424/429 |
| 4,787,732 A | * | 11/1988 | Siviglia | ...................... 351/160 R |
| 4,952,045 A | * | 8/1990 | Stoyan | ....................... 351/160 R |
| 6,780,176 B2 | | 8/2004 | Hasegawa | |
| 2003/0056281 A1 | | 3/2003 | Hasegawa | |
| 2006/0132707 A1 | * | 6/2006 | Tung | .......................... 351/160 R |
| 2006/0152673 A1 | * | 7/2006 | Cotie et al. | ................. 351/160 H |

FOREIGN PATENT DOCUMENTS

| | | |
|---|---|---|
| JP | 2003-93431 | 4/2003 |
| JP | 2003-135511 | 5/2003 |
| JP | 2004-350803 | 12/2004 |

* cited by examiner

*Primary Examiner* — Melanie Hand
*Assistant Examiner* — Andrew S Lo
(74) *Attorney, Agent, or Firm* — Michael J. Striker

(57) ABSTRACT

A jig and a cooling fluid injection tool are provided for use in the correction of corneal shape of an eyeball. Correction of the eyeball takes place while the cornea is warmed. The jig includes a shape retention part of a sucking disc configuration having an inner surface side that contacts the eyeball and a grip part formed on an outer surface side of the shape retention part. An inner surface-sided cornea contacting section of the shape retention part is flattened and a cooling fluid injection hole passing through the grip part is formed in the center of the shape retention part with a diameter large enough for a wearer to see outside.

3 Claims, 6 Drawing Sheets

VISION CORRECTIVE JIG AND COOLING FLUID INJECTION TOOL FOR THE JIG

CROSS-REFERENCE TO RELATED APPLICATIONS

The invention described and claimed hereinbelow is also described in International Application No. PCT/JP2008/059668, filed on May 26, 2008, which takes its basis from Japanese Patent Application 2008-006430, filed on Jan. 16, 2008. This Japanese Patent Application, whose subject matter is incorporated herein by reference, provides the basis for a claim of priority of invention under 35 U.S.C. 119(a)-(d).

TECHNICAL FIELD

The present invention relates to a vision corrective jig for reshaping a cornea of an eyeball and restoring vision and to a cooling fluid injection tool used for the vision corrective jig.

BACKGROUND ART

Previously, as a vision corrective therapy for such as myopia, hyperopia, and astigmatism, a method in which a contact lense with a special shape worn during sleep corrects a cornea to the predetermined shape (Ortho-Keratology) has been known. The method has a problem that the corrected vision can be retained for a certain period after removal of the lense, the cornea, however, resumes thereafter its previous shape due to the corneal spring-back effect. In addition, a treating method called LASIK which removes a part of a cornea with laser beam is known. The method also has some problems, that is, it requests high surgical techniques from the operating ophthalmologist, it is highly risky and gives a large psychological burden.

Accordingly, the present inventor has proposed a new treating method which can reshape without injuring a cornea and restore vision and makes the reshaped cornea impossible to resume its previous shape due to the corneal spring-back effect, as well as an eyesight correcting apparatus (Patent Document 1). The apparatus comprises a cap-like cornea sucking member furnished with a slidably attached cornea pressure member, and an air sucking port and an ophthalmic solution injection port. The apparatus warms and softens the cornea with the predetermined method, then while sucking the cornea with sucking force caused through the air sucking port, corrects the cornea to the predetermined shape by the cornea pressure member, immediately thereafter quenches the cornea by introducing a cooling liquid through the ophthalmic solution injection port and thereby fixes the corneal shape.

Additionally, the present inventor has proposed a new eye mask which warms and softens a cornea as described above, also is effective for recovering from asthenopia and disordered ocular functions (Patent Document 2). This eye mask is provided with self-heating warming members in the mask body, as well as eye pads on the portions corresponding to the eyeball parts in which magnetic materials and vibrators are attached by insertion, and warms the eyeball to the predetermined temperature, and gives magnetic force and microvibration when needed.

Furthermore, as improved alternatives of the eyesight correcting apparatus and the eye mask described above, the present inventor has proposed a hand-type cornea corrective jig in which a head portion is warmed by a heating means, a cornea cooling jig which squirts a cooling fluid in a ring shape with a cylinder and a piston, an eye mask provided with eye pads which are filled with gelatinous materials at eye portions, and the like (Patent Document 3).

Patent Document 1: Japan Patent Laid-Open Publication No. 2003-135511
Patent Document 2: Japan Patent Laid-Open Publication No. 2003-93431
Patent Document 3: Japan Patent Laid-Open Publication No. 2004-350803

DISCLOSURE OF INVENTION

Problems to be Solved by the Invention

After continued study, I found that the vision corrective jigs have some problems as a matter of practicality, respectively. That is, the eyesight correcting apparatus of Patent Document 1 has problems that it has a complicated structure and is hard to handle, and the vision corrective jig and the cornea cooling jig of Patent Document 3 have a problem that the desired cite is hardly treated accurately because they being in hands of the operating ophthalmologist press or cool.

The present invention has been proposed in order to solve problems described above, and its object is to provide a vision corrective jig and a cooling fluid injection tool for the vision corrective jig, which can, in performing vision corrective treatment to reshape a cornea while the cornea of the eyeball is warmed and softened, then quench the reshaped cornea, correct the cornea to the predetermined shape accurately and easily, as well as, have simple structures and are easily handled, and may be manufactured at low cost.

Means for Solving Problems

The vision corrective jig of the present invention which has been proposed in order to solve problems described above is characterized in that it is a jig that wraps an eyeball and reshapes a cornea softened by warming, comprises a shape retention part of sucking disc configuration with its inner surface side contacting with the eyeball and a grip part formed on the outer surface side of the shape retention part, and the inner surface-sided cornea contacting section of the shape retention part is flattened and a cooling fluid injection hole passing through the shape retention part and the grip part is formed.

Such a vision corrective jig is effective for treatment of myopia, and can correct a forwardly poked cornea to normal shape by pressing with the flattened cornea contacting section. The area of the flat portion of the cornea contacting section may be selected depending on the degree of myopia, the age of the patient, and the like. When wrapping an eyeball, the vision corrective jig can be attached accurately to the predetermined site by holding the grip part between tips of fingers. The cooling fluid includes cooling water, cooling air, cooling medical solutions, and the like (the same shall apply hereinafter). The vision corrective jig is made of materials being harmless to human bodies such as glass, synthetic resins (for example, hard acrylic resin), and metals, and when glass or a synthetic resin is used, it may be transparent or translucent.

The present invention is characterized in that the cooling fluid injection hole is formed at the central areas of the shape retention part and the grip part, and its diameter is large enough for the wearer to see outside through the cooling fluid injection hole.

Such a configuration, when the eyeball is wrapped by the vision corrective jig, allows the wearer (the patient) to see an outside target and to confirm that the vision corrective jig is attached to the exact position.

In addition, the present invention is characterized in that the cooling fluid injection hole is formed with the grip part-sided diameter is larger than the shape retention part-sided diameter.

This configuration allows the operating ophthalmologist to look through the grip part-sided hole with larger diameter and to confirm that the vision corrective jig is attached to the exact position of the cornea, and also allows a discharge tube provided at the tip of a cooling fluid injection tool described later to be inserted into the vision corrective jig easily and accurately.

Furthermore, the present invention is characterized in that the grip part is integrally formed on the outer surface side of the shape retention part in a button shape.

Such a configuration makes integral molding of the shape retention part and the grip part possible, formation of the cooling fluid injection hole with the predetermined shape easy, the whole appearance shape compact, and the action with holding the grip part between tips of fingers easy.

When a cornea is heated, softened, and corrected by using the vision corrective jig for myopia described above, by extracting a cooling fluid through the cooling fluid injection hole of the vision corrective jig, the cornea must be quenched and thereby the reshaped cornea must be fixed. The cooling fluid injection tool of the present invention used for this purpose is characterized in that it comprises a compression transport part enabling filling and compression transport of the cooling fluid, and a discharge tube provided at the tip of the compression transport part and being insertable into the cooling fluid injection hole of the vision corrective jig.

Such a cooling fluid injection tool allows the discharge tube to be inserted into the cooling fluid injection hole of the vision corrective jig, a proper amount of a cooling fluid filled in the compression transport part such as cooling water and cooling air to be extracted from the discharge tube toward the exact cite of the cornea.

In addition, the cooling fluid injection tool of the present invention is characterized in that the compression transport part consists of a cylinder and a piston, and the compression transport part is a compression pump.

A cooling fluid injection tool with such a configuration is simple in structure, may be manufactured at low cost, and is easy in handling.

By the way, the vision corrective jig of the present invention which has been proposed in order to solve problems described above is characterized in that it is a jig that wraps a eyeball and reshapes a cornea softened by warming, comprises a shape retention part of sucking disc configuration with its inner surface side contacting with the eyeball and a grip part formed on the outer surface side of the shape retention part, and the inner surface of the shape retention part is formed in a spherical shape after the eyeball, as well as, a packing member is attached by insertion in the grip part, and the cooling fluid injection hole passing through the packing member and the shape retention part is formed.

Such a vision corrective jig is effective for treatment of hyperopia, and can correct a backwardly retracted cornea to normal shape by applying negative pressure through the cooling fluid injection hole to the cornea and pull the cornea forwardly and making contact with the spherical surface of the shape retention part. The packing member can keep a suction tube and the like for applying negative pressure in a air tight state. The packing member may be detachably attached to the vision corrective jig, and may be attached by insertion to the vision corrective jig when needed. The spherical surface of the shape retention part may be selected depending on such as the degree of hyperopia and the age of the patient. When wrapping an eyeball, the vision corrective jig can be attached accurately to the predetermined site by holding the grip part between tips of fingers. The vision corrective jig, in the same way as described above, is made of materials being harmless to human bodies such as glass, synthetic resins (for example, hard acrylic resin), and metals, and when glass or a synthetic resin is used, it may be transparent or translucent.

Additionally, the present invention is characterized in that the cooling fluid injection hole is formed at the central areas of the packing member and the shape retention part, and its diameter is large enough for the wearer to see outside through the cooling fluid injection hole. Such a configuration, in the same way as described above, allows the wearer to confirm that the vision corrective jig is attached to the exact position. The cooling fluid injection hole formed in the packing member has a diameter that allows firmly attachment to the suction tube for applying negative pressure to the cornea. This configuration, when applying negative pressure to the cornea, can prevent air leak from the packing member. Furthermore, the vision corrective jig may be firmly attached to the surface of the eyeball by applying a binder being harmless to human bodies on the circumference end surface of the shape retention part of the vision corrective jig.

Furthermore, the present invention is characterized in that the grip part is integrally formed on the outer surface side of the shape retention part in a long-bodied button shape.

Such a shape of the grip part allows the packing member to be attached by insertion in the grip part, and makes integral molding of the shape retention part and the grip part possible, the whole appearance shape compact, and the action with holding the grip part between tips of fingers easy.

When a cornea is heated, softened, and corrected by using the vision corrective jig for hyperopia described above, by extracting a cooling fluid through the cooling fluid injection hole, the cornea must be quenched and thereby the reshaped cornea must be fixed. The cooling fluid injection tool of the present invention used for this purpose is characterized in that it comprises a compression transport part enabling filling and compression transport of the cooling fluid, and a discharge tube provided at the tip of the compression transport part, and a flow dividing member for squirting the cooling fluid in a ring shape is provided in the discharge tube.

Such a configuration makes it possible that, avoiding the forwardly pulled the central part of the cornea by negative pressure, the circumference end surface of the cornea is intensively quenched and the central part of the cornea is made impossible to resume the previous shape, and the reshaped cornea is fixed.

The present invention is also characterized in that the flow dividing member is an insert tube having a conically shaped rear end, and a cooling fluid flowing pass is formed between the insert tube and the discharge tube.

Such a simple configuration allows the cooling fluid to be evenly squirted in a ring shape.

Additionally, the present invention is characterized in that the compression transport part consists of a cylinder and a piston. A cooling fluid injection tool with such a configuration is simple in structure, may be manufactured at low cost, and is easy in handling.

The vision corrective jig of the present invention is characterized in that it is a jig that wraps an eyeball and reshapes a cornea softened by warming, comprises a shape retention part of sucking disc configuration with its inner surface side contacting with the eyeball and a grip part formed on the outer surface side of the shape retention part, and the inner surface of the shape retention part is formed in a spherical shape after the eyeball, as well as, another spherical concave portion is formed in the center of the inner-sided surface, and a cooling fluid injection hole passing through the shape retention part and the grip part is formed.

Such a vision corrective jig is effective for treatment of relatively mild hyperopia with soft corneal tissue, and when a slightly and backwardly retracted cornea is warmed and softened, then the eyeball is wrapped by the vision corrective jig, the cornea bulges out after the concave portion formed in the center of the inner-sided surface of the shape retention part. If the cornea in this situation is quenched, its bulged part contracts slightly, and it is corrected to a normal shape. Accordingly, when using this vision corrective jig for hyperopia is used, the cornea suction is not needed, and treatment of hyperopia becomes easy.

Effect of the Invention

The vision corrective jig and the cooling fluid injection tool of the present invention described above show the effects that, in performing vision correction treatment of a cornea of an eyeball to warm, soften, and reshape, then quench and fix, the cornea can be corrected to the predetermined shape accurately, and easily, as well as, the jig and the tool are simple in structures, handled easily, and can be manufactured at low cost. Each invention of the claims shows the effects described above.

EXPLANATIONS OF LETTERS OR NUMERALS 1 is a vision corrective jig for myopia;
2 is its shape retention part;
2a is its cornea contact area;
2b is its circumference end surface;
3 is its grip part;
4 is its cooling fluid injection hole;
10 is a vision corrective jig for hyperopia;
12 is its shape retention part;
12a is its cornea contact area;
12b is its circumference end surface;
13 is its grip part;
14 is its packing part;
15 is its cooling fluid injection hole;
20 is a cooling fluid injection tool;
24 is its discharge tube;
30 is another cooling fluid injection tool;
33 is its discharge tube;
40 is still another cooling fluid injection tool;
43 is its discharge tube;
44 is its insert tube;
45 is its flowing pass;
50 is another vision corrective jig for hyperopia;
52 is its shape retention part;
52a is its concave part;
53 is its grip part; and
54 is its cooling fluid injection hole.

BEST MODES FOR CARRYING OUT THE INVENTION

Figure 1:
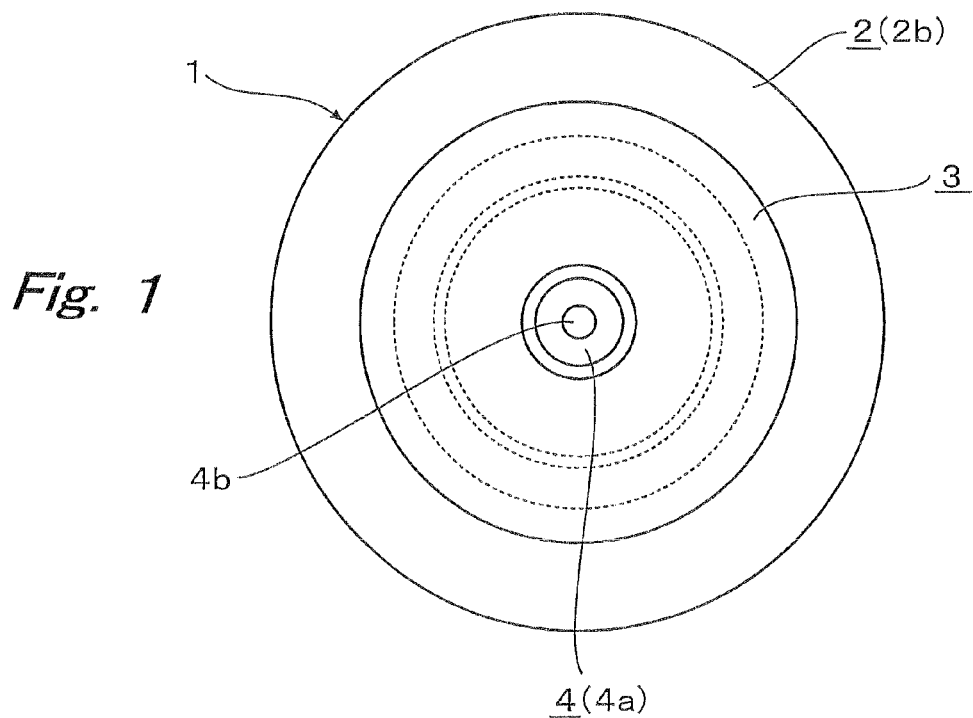
FIG. 1 is a plan view of a vision corrective jig for myopia of the present invention.
Figure 2:
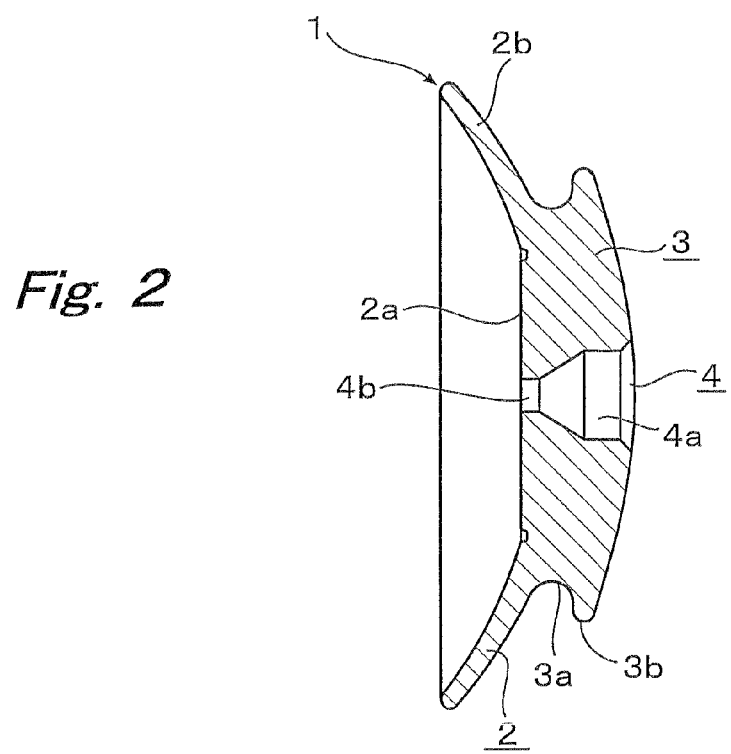
FIG. 2 is a sectional view of the same.

In what follows, embodiments of the present invention will be described with reference to the attached drawings. FIGS. 1 and 2 show a vision corrective jig suitable for treatment of myopia, and FIG. 1 is its plan view and FIG. 2 is its sectional view. This vision corrective jig for myopia 1 is used by attaching to an eyeball in the same way as a hard contact lens.

The vision corrective jig for myopia 1 is wholly in a disc shape, and comprises a shape retention part 2 of sucking disc configuration and a grip part 3 in a button shape formed on the outer surface side of the shape retention part. This vision corrective jig for myopia 1 is made of materials being harmless to human bodies such as glass, metals, and synthetic resins, and the shape retention part 2 and the grip part 3 are integrally molded.

As shown in FIG. 2, the cornea contact area 2a in the center of the inner side (eyeball-sided) surface of the shape retention part 2 is flattened, and the inner surface of the circumference end surface 2b is formed in a spherical shape. A body section 3a of the grip part 3 is narrow in the middle, thereby a flange section 3b to be caught by fingers is formed. In the central areas of the shape retention part 2 and the grip part 3, the cooling fluid injection hole 4 passing through them is formed.

The cooling fluid injection hole 4 corresponds to tip shapes of cooling fluid injection tools 20 and 30 described later, and in this case, and the hole 4 is formed with multiple stages so that a grip part-sided hole 4a has a larger diameter than that of a shape retention part-sided hole 4b. In addition, as described later, when the vision corrective jig for myopia 1 wraps an eyeball of the patient, the cooling fluid injection hole 4 has a diameter large enough for the wearer (the patient) to see outside landscape or the target through the cooling fluid injection hole 4. This configuration allows an operating ophthalmologist to look through the grip part-sided hole 4a to confirm that the vision corrective jig for myopia 1 is attached to the predetermined position of the eyeball (cornea) accurately. Not limiting specifically, but in this case, the diameter of the shape retention part-sided hole 4b is 5 mm to 8 mm, and that of the grip part-sided hole 4a is 12 mm to 20 mm.

Many types of vision corrective jig for myopia 1 with different areas of the cornea contact area 2a of the shape retention part 2, that is, the flat portion must be prepared. That is, in cases of mild myopia, the jig with a smaller flat portion is used, and in cases of severe myopia, the jig with a larger flat portion is used. Additionally, in order to address various patients with different signs, ages, and the like, various types of vision corrective jig for myopia 1 with such as different curvatures of the circumference end surface 2b and diameters of the cooling fluid injection hole 4 should be prepared.

Figure 3:
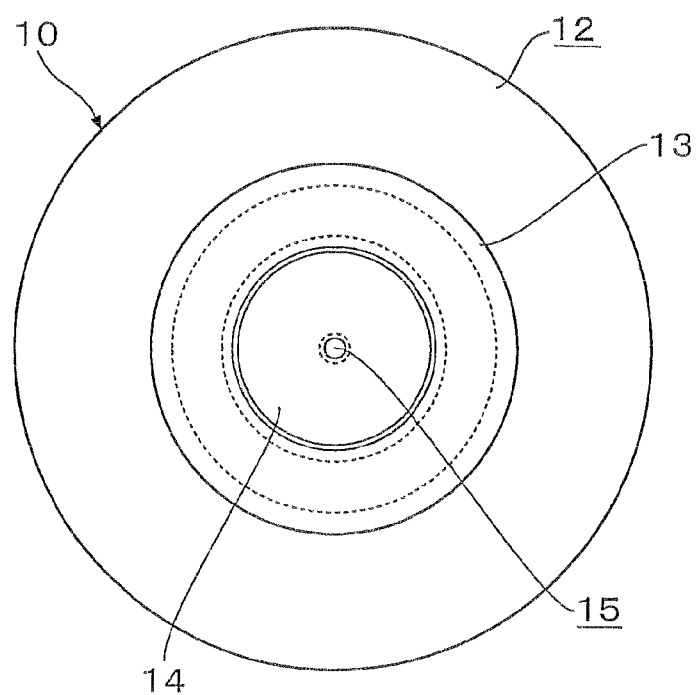
FIG. 3 is a plan view of a vision corrective jig for hyperopia of the present invention.
Figure 4:
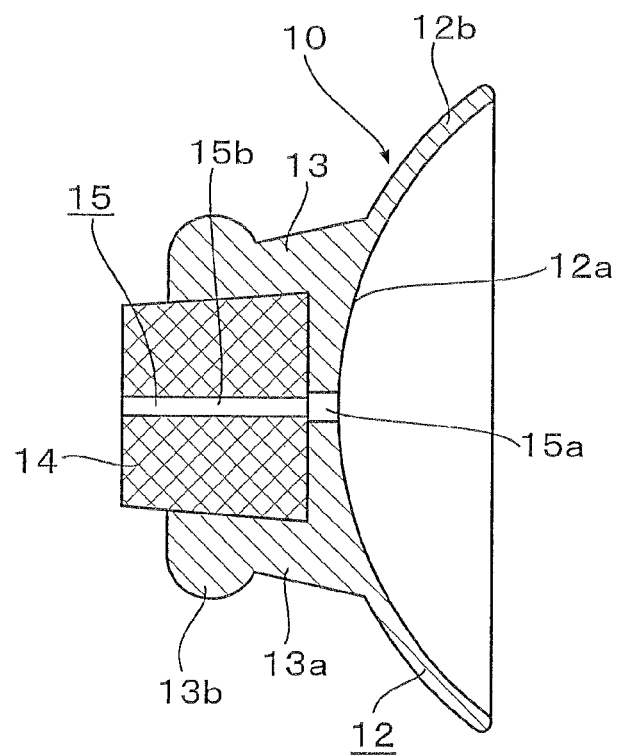
FIG. 4 is a sectional view of the same.

By the way, FIGS. 3 and 4 show a vision corrective jig suitable for treatment of hyperopia, and FIG. 3 is its plan view and FIG. 4 is its sectional view. This vision corrective jig for hyperopia 10 is also used by attaching to an eyeball in the same way as a hard contact lens.

The vision corrective jig for hyperopia 10 is wholly in a disc shape, and comprises a shape retention part 12 of sucking disc configuration and a grip part 13 in a long-bodied button shape formed on the outer surface side of the shape retention part. This vision corrective jig for hyperopia 10 is, in the same way as described above, made of materials being harmless to human bodies such as glass, metals, and synthetic resins, and the shape retention part 12 and the grip part 13 are integrally molded.

As shown in FIG. 4, the shape retention part 12 has the cornea contact area 12a and the circumference end surface 12b both formed with the uniform curvature in a spherical shape on the inner surface side (the eyeball side). Also, in a body section 13a of the grip part 13, the packing member 14 made of an elastic material such as rubber and a soft resin is attached by insertion. In this case, the packing member 14 is attached by insertion with its rear-end projected from the rear-end 13b of the grip part 13 so that a suction tube for applying negative pressure to the cornea described later can be held closely in a long span, and may be detached from the vision corrective jig for hyperopia 10 by holding the rear-end and pulling when needed.

In the center of the shape retention part 12, the cooling fluid injection hole 15 passing through the packing member 14 and the shape retention part 1 is formed. Its packing member-sided hole 15b has a diameter that is attached air-tightly to the suction tube described above due to elasticity of the packing member, and its shape retention part-sided hole 15a has a slightly larger diameter than that of the packing member-sided hole 15b and a discharge tube 43 of a cooling fluid injection tool 40 described later can be inserted.

When the vision corrective jig for hyperopia 10 wraps an eyeball of the patient, the cooling fluid injection hole 15 has a diameter large enough for the wearer to see outside landscape or the target through the cooling fluid injection hole 15. In addition, when needed, the operating ophthalmologist can detach the packing member 14 and look through the shape retention part-sided hole 15a to confirm that the vision corrective jig for hyperopia 10 is attached to the predetermined position of the eyeball (cornea) accurately. Not limiting specifically, but in this case, the diameter of the packing member-sided hole 15b is 5 mm to 8 mm, and that of the shape retention part-sided hole 15a is 7 mm to 15 mm.

In order to address various patients with mild or severe hyperopia, various types of vision corrective jig for hyperopia 10 with such as different inner sided curvatures of the shape retention part 12 and diameters of the cooling fluid injection hole 15 should be prepared.

Figure 5:
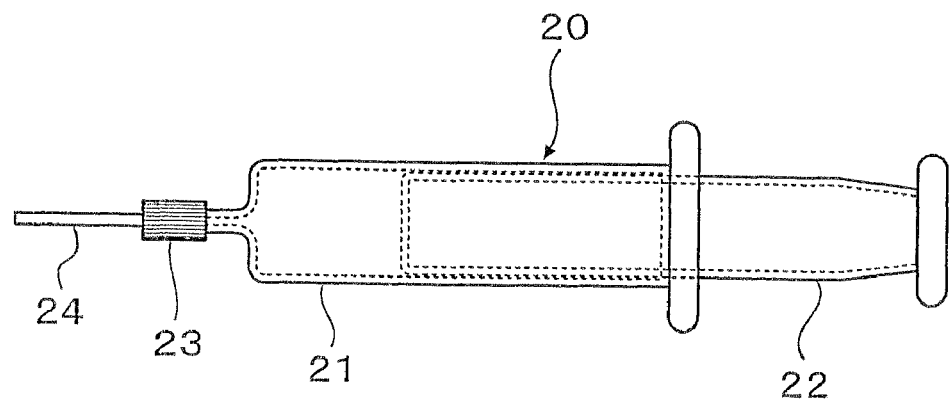
FIG. 5 is a plan view of a cooling fluid injection tool used for a vision corrective jig for myopia of the present invention.
Figure 6:
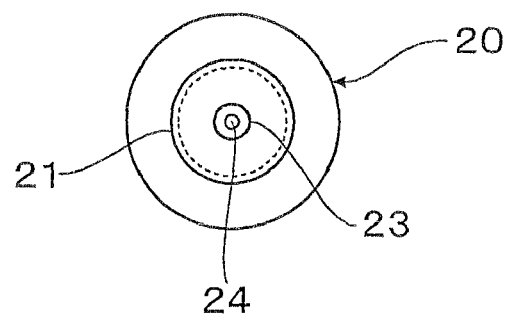
FIG. 6 is a left side view of the same.

FIGS. 5 and 6 show a cooling fluid injection tool used for the vision corrective jig for myopia 1 described above, and FIG. 5 is its plan view and FIG. 6 is its left side view. This cooling fluid injection tool 20 comprises a cylinder 21 and a piston 22 both being a compression transport part of a fluid, and a discharge tube 24 with a small diameter is detachably attached to the tip of the cylinder 21 through a connection cap 23. The cooling fluid injection tool 20 is made of such as synthetic resins, metals, and glass.

Figure 7:
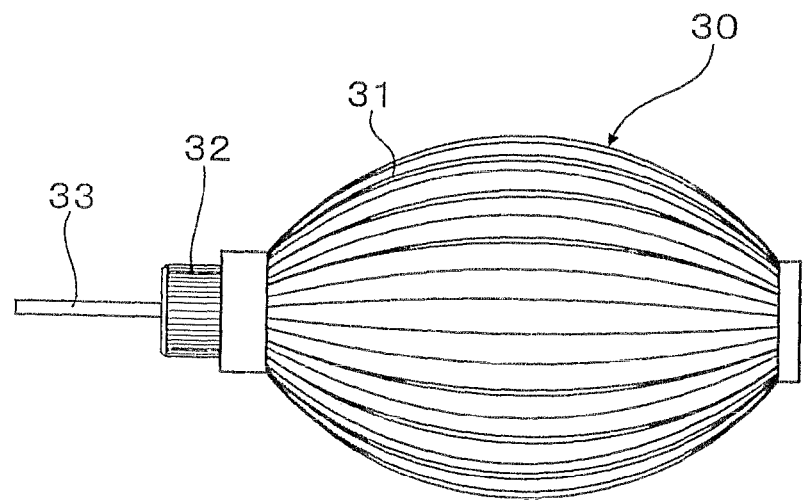
FIG. 7 is a plan view of another cooling fluid injection tool used for a vision corrective jig for myopia of the present invention.
Figure 8:
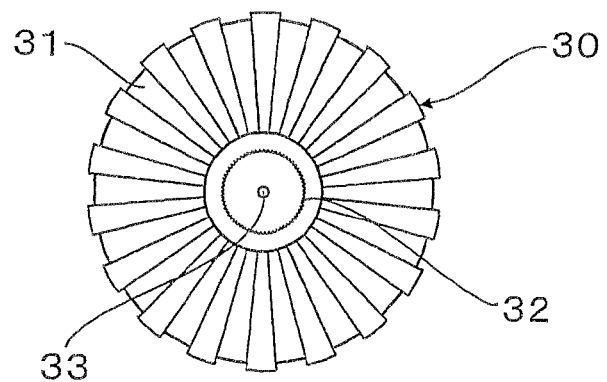
FIG. 8 is a left side view of the same.

FIGS. 7 and 8 show another cooling fluid injection tool used for the vision corrective jig for myopia 1, and FIG. 7 is its plan view and FIG. 8 is its left side view. This cooling fluid injection tool 30 comprises a compression pump 31 being a compression transport part of a fluid, and a discharge tube 33 with a small diameter to be attached to the tip of the compression pump 31 through a connection cap 32. In this case, the compression pump 31 is configured wholly in an oval-spherical shape and in bellows-like shape in circumferential directions by using such as soft synthetic resins and rubber. The discharge tube 33 is made of such as metals, synthetic resins, and glass.

Figure 9:
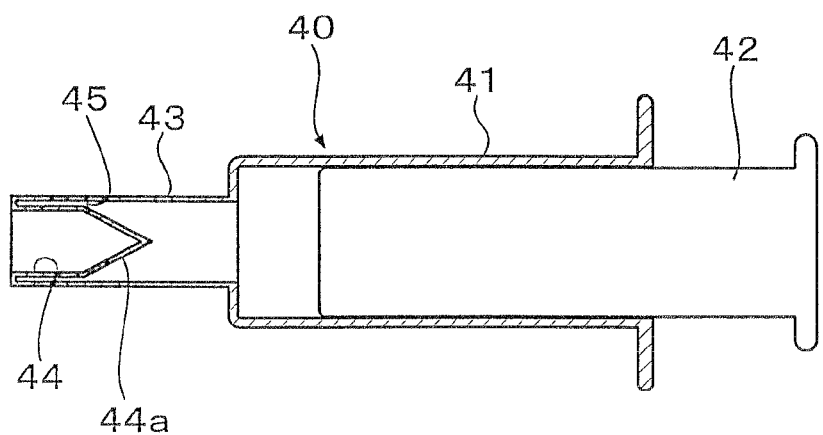
FIG. 9 is a sectional view of a cooling fluid injection tool used for a vision corrective jig for hyperopia of the present invention.
Figure 10:
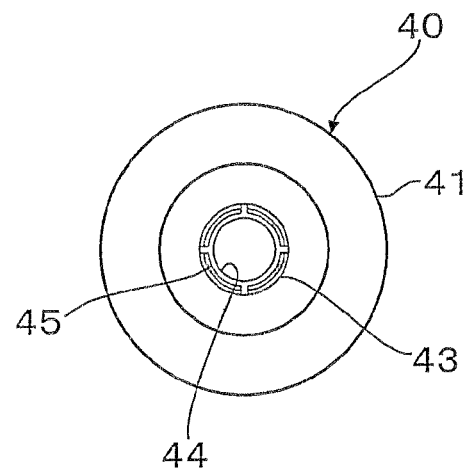
FIG. 10 is a left side view of the same.

FIGS. 9 and 10 show a cooling fluid injection tool used for the vision corrective jig for hyperopia 10, and FIG. 9 is its plan view and FIG. 10 is its left side view. This cooling fluid injection tool 40 comprises a cylinder 41 and a piston 42 both being a compression transport part, and a discharge tube 43 with a small diameter is projected at the tip of the cylinder 41.

In the tip of the discharge tube 43, an insert tube 44 is attached, and a ring-like cooling fluid flowing pass 45 is formed in the hollow between the inner face of the discharge tube 43 and the outer face of the insert tube 44. The insert tube 44 is a cylinder whose tip section is open and whose rear-end section 44a is formed in a conical shape, and is fixed with intervals by such as support ribs and spot welding to the inner surface of the discharge tube 43. The cooling fluid injection tool is made of such as synthetic resins, metals, and glass.

Next, vision corrective treating methods utilizing vision corrective jigs and cooling fluid injection tools described above are explained. Firstly, in case of myopia treatment, an operating ophthalmologist performs vision tests and measures the patient's left and right visions, respectively, then examines whether or not each cornea has any abnormality, and takes photos of front and side views and any other needed cites of both cornea. These results are fundamental data for the vision corrective treatment. Depending on the diagnosis, vision corrective jigs for myopia 1 with suitable shapes of the shape retention part 2 corresponding to the degrees of myopia of left and right eyes are prepared.

In the beginning of the treatment, the eyeball is warmed to the predetermined temperature (for example, 39° C. to 45° C.), and the keratinous cornea is sufficiently softened. The warming temperature is suitably selected based on the hardness of the cornea with consideration of the age and degree of myopia of the patient. The required warming time is, for example, 13 minutes to 20 minutes.

As the warming method, not limiting specifically, but eye masks and the like proposed by the present inventor and published as Japan Patent Laid-Open Publications No. 2003-93431 and No. 2004-350803 may be used. If a special eye mask is not used, however, the cornea may be softened by, for example, warming with a heater utilizing a known apparatus, warming with steam-spraying from a steam generator, or by commercially available warming pads and the like.

In cases of abnormally hardened cornea, aged cornea, and thickened cornea, the hardened portion of cornea may be intensively softened by spurting warm wind at predetermined temperature from such as a small gas burner, a small hair dryer, or another warm wind generating apparatus through a micro nozzle.

After the cornea is sufficiently softened, when needed, a binder is applied to the inner surface-sided (the eyeball contact section-sided) peripheral section of the shape retention part 2 of the vision corrective jig for myopia 1, the cornea is wrapped by the jig 1 by griping the grip part 3 and fixed so as not to be moved. As the binder, materials being harmless to human bodies such as water-soluble gelatin glue, starch glue, and hyaluran glue may be used.

After the cornea is wrapped by the vision corrective jig for myopia 1, the patient looks outside landscape, light, an optometry table, and the like through the cooling fluid injection hole 4 of the vision corrective jig for myopia 1 and confirms that the vision corrective jig for myopia 1 is attached to the central cite of the pupil. When needed, the operating ophthalmologist also peers into the cooling fluid injection hole 4 from outer side of the grip part 3 and confirms the attached cite of the vision corrective jig 1. After the completion of confirmation, the cornea is warmed for the predetermined time over the eyelid of the patient by using such as an eye mask, a heater, and a steam generator described above.

And by that, the cornea is reshaped after the inner surface shape of the shape retention part 2 of the vision corrective jig for myopia 1. That is, by the flattened cornea contact area 2a of the vision corrective jig for myopia 1, in general spherically poked forward myopic cornea is compressed to the direction of the crystalline lens, and the keratinous cornea is reshaped so that an image at the near/far point is accurately displayed on the retina.

By the way, in above case, warming and softening procedure of the cornea is performed before and after the eyeball is wrapped by the vision corrective jig for myopia 1, however, when needed, either of before and after warming and softening procedure may be omitted.

Next, if it is considered that the cornea is sufficiently softened and reshaped, the warming and softening procedure described above is discontinued, the vision corrective jig for myopia 1 attached to the eyeball is cooled naturally at room temperature for the predetermined time (for example, 5 minutes to 10 minutes), and when the temperature of the vision corrective jig for myopia 1 reaches near the body temperature, the vision corrective jig for myopia 1 is detached from the eyeball. After the confirmation of the eye to be at ease and stabilized, vision tests with the naked eye because the cornea is already corrected. As the result of the vision tests, if it is confirmed that the vision is not restored to the desired vision by the patient, the corneal treatment procedure described above is repeated.

If it is confirmed that the vision is restored, the treatment to stabilize and fix the reshaped cornea is performed. The vision corrective jig for myopia 1 detached from the eyeball is sterilized, again attached to the patient's eyeball accurately, and the cornea of the eyeball is warmed by the method described above. Since the cornea is already corrected, although individual differences exist, warming for, for example, 6 minutes to 10 minutes may be sufficient.

After the cornea is sufficiently softened, cooling water (or cooling wind, the same shall apply hereinafter) is injected from the cooling fluid injection hole 4 of the vision corrective jig for myopia 1 and quenches the cornea. In the warmed and softened cornea, the keratinous cellular tissues are relaxed and their volume expansion is caused. By quenching them instantly, corneal cellular tissues contract instantly, and the reshaped cornea is stabilized and fixed, and thereby the reshaped cornea never resume thereafter its previous shape even if the corneal spring-back effect occurs. This quenching procedure resembles the hardening procedure of a metal structure by quench hardening for hard materials such as metals.

The corneal quenching procedure must be performed immediately after the cornea is warmed and softened, and if time passes, fixing of the cornea becomes difficult.

In quenching the cornea, a cylinder-type cooling fluid injection tool 20 shown in FIGS. 5 and 6, or a compression pump-type (dropper-type) cooling fluid injection tool 30 shown in FIGS. 7 and 8 may be used. Cooling water is beforehand cooled to the predetermined temperature (for example, +1° C. to +4° C. for cooling water, −10° C. to +2° C. for cooling wind) in a refrigerator and the like. It is recommended that the cooling fluid injection tools 20 and 30 are also cooled beforehand in a refrigerator and the like.

In case of the cooling fluid injection tool 20, by pulling the piston 22, cooling water is sucked into the cylinder 21 from the discharge tube 24, and in case of the cooling fluid injection tool 30, by pumping the compression pump 31, cooling water is sucked into the compression pump 31 from the discharge tube 33. Then, the discharge tubes 24 and 33 of the cooling fluid injection tools 20 and 30 are inserted into the cooling fluid injection hole 4 of the vision corrective jig for myopia 1, the piston 22 is pushed or the compression pump 31 is compressed, and inside cooling water is extracted toward the cornea (the extracted amount is, for example, approximately 1 cm$^3$ to 15 cm$^3$).

Additionally, for quenching the cornea, not limited to the cooling fluid injection tool 20 described above, any fluid cooling apparatus for exclusive use may be prepared and a cooling fluid may be sprayed through the cooling fluid injection hole 4 of the vision corrective jig for myopia 1.

After completion of the corneal quenching and hardening procedure, the cooling fluid injection tool 20 or 30 and the vision corrective jig for myopia 1 are detached from the eyeball, the eyeball is washed, and the treatment is completed. Then, the operating ophthalmologist performs vision tests to confirm that the cornea is corrected as desired by the patient, takes photos of front and side views and any other needed cites of the corrected cornea, gives the patient a set and keeps a set with the medical record. Thereby, a series of vision corrective treatment is finished.

Secondly, treatment of hyperopia including presbyopia is explained. In cases of hyperopia, the patients are in general the aged. Before treatment, the operating ophthalmologist examines the condition of the eyeball of the patient, whether the condition is that of axial hyperopia, whether the eyeball is depressed backward and becomes flat, and the like, and diagnoses beforehand whether the cornea may be corrected.

The operating ophthalmologist measures the patient's left and right visions, respectively, then examines whether or not each cornea has any abnormality, and takes photos of front and side views and any other needed cites of the cornea. These results are fundamental data for the vision corrective treatment. Depending on the diagnosis, vision corrective jigs for hyperopia 10 with suitable shapes of the shape retention part 2 corresponding to the degrees of hyperopia of left and right eyes are prepared.

In the beginning of the treatment, the eyeball is warmed with the same method used in the myopia correction treatment described above, and the cornea is softened. The warming temperature and time may be the same as that for myopia treatment, but, since the major patients are aged and corneal hardening is generally progressed, a little higher temperature and a little longer time are preferable.

After the cornea is sufficiently softened, when needed, a binder is applied to the inner surface-sided peripheral section of the circumference end surface 12b of the shape retention part of the vision corrective jig 10, the cornea is wrapped by the jig 10 by griping the grip part 13 and fixed so as not to be moved. It is needed that the shape retention part 12 is closely attached to the eyeball by the binder so that air leakage is not occurred during the suction procedure described later.

After the cornea is wrapped by the vision corrective jig for hyperopia 10, the patient looks outside landscape, light, an optometry table, and the like through the cooling fluid injection hole 15 of the vision corrective jig 10, and confirms that the vision corrective jig 10 is attached to the central cite of the pupil. When needed, the operating ophthalmologist peers from the shape retention part-sided hole 15a with detached packing member 14 and confirms that the vision corrective jig 10 is attached to the predetermined cite. After the completion of confirmation, the cornea is warmed for the predetermined time over the eyelid of the patient.

Hyperopia is generally the condition where axial lengths of the eyeball sclera and choroid are short, and often includes the hollow cornea. Therefore, a suction tube (not shown in Figures) connected with a suction apparatus is inserted into the vision corrective jig for hyperopia 10 from the packing member 14 side through the cooling fluid injection hole 15, applies negative pressure to the inner surface of the shape retention part 12, and pulls forward the cornea. By keeping this situation for the predetermined time (for example, 13 minutes to 20 minutes), the cornea is corrected to the shape after the inner surface of the shape retention part 12.

The suction apparatus is not particularly limited so long as it provides sufficient suction force to pull forward the cornea, and a known suction cylinder and the like may be used, however, in order to address various signs of patients, an apparatus with adjustable suction force is preferable. The suction tube connected with the suction apparatus is made of such as metals, synthetic resins, and rubber, and is inserted into the cooling fluid injection hole 15$b$ of the packing member 14 in an air tight status.

If it is considered that the cornea is reshaped, the warming and softening procedure is discontinued, the vision corrective jig for hyperopia 10 is cooled to near the body temperature, the vision corrective jig 10 is detached from the eyeball. Vision tests with the naked eye are performed. If it is confirmed that the vision is not restored to the desired vision by the patient, the corneal treatment procedure described above is repeated by such as replacing to another vision corrective jig for hyperopia 10 with different shape of the shape retention part 12, or raising warming temperature.

If it is confirmed that the vision is restored, the treatment to stabilize and fix the reshaped cornea is performed. The vision corrective jig for hyperopia 10 detached from the eyeball is sterilized, again attached to the patient's eyeball accurately, and the cornea of the eyeball is warmed by the method described above.

The cornea is sufficiently softened and quenched, however, being different from the myopic corrective treatment, if the central part of the softened cornea is quenched, the convex cellular tissues in the central part of the cornea caused by negative pressure may contract and harden, and the convex part may be flattened. Therefore, in hyperopic treatment, a cooling fluid injection tool 40 shown in FIGS. 9 and 10 is used.

In case of the cooling fluid injection tool 40, by pulling the piston 42, cooling water already cooled to the predetermined temperature in a refrigerator and the like as described above is sucked into the cylinder 41 from the discharge tube 43, and the discharge tube 43 is inserted into the cooling fluid injection hole 15 of the vision corrective jig for hyperopia 10. If the packing member 14 disturbs, it may be removed from the vision corrective jig for hyperopia 10, and the discharge tube 43 may be directly inserted into the shape retention part-sided hole 15$a$.

When, by pushing the piston 42, inside cooling water is extracted toward the cornea, the cooling water is passed through the cooling fluid flowing pass 45 between the insert tube 44 and the discharge tube 43, squirted in a ring shape, and quenches intensively the peripheral part except for the central part of the cornea. Thereby, in the same way described above, corneal cellular tissues in the peripheral part contract instantly, and the reshaped cornea is stabilized and fixed, and thereby the reshaped cornea never resume thereafter its previous shape even if the corneal spring-back effect occurs.

After completion of the corneal quenching and hardening procedure, the cooling fluid injection tool 40 and the vision corrective jig for hyperopia 10 are detached from the eyeball, the eyeball is washed, and the treatment is completed. The following procedure is the same as that for myopic treatment. The cooling fluid injection tool 40 for hyperopia corrective treatment is not limited to that described above, and any fluid cooling apparatus for exclusive use may be prepared and by using a nozzle squirting in a ring shape for exclusive use, a cooling fluid may be squirted toward the cornea from the cooling fluid injection hole 15.

In case of hyperopia corrective treatment, being different from myopia corrective treatment, the objective is mostly the aged, the degree of corneal hardening is different for each patient, and vision correction in short time is often difficult. Accordingly, not correction in once but several times of correction with suitable intervals is preferable.

Next, corrective treatment of astigmatism is explained. Astigmatism is a condition where the front part of the cornea, or the corneal part over the iris (black eye) is not in a normal conical shape. That is, since this conical part includes concave and convex portions, or in an elliptic or oval shape, the image displayed on the retina is blur or distorted. The correction of this astigmatism only can be performed by using a corneal corrective jig for correcting to normal corneal shape used in corrective treatment of myopia and hyperopia.

However, since astigmatism is actually combined with myopia or hyperopia, by performing corrective treatment of not astigmatism only but myopia or hyperopia, the cornea is corrected to a normal shape. Accordingly, except for special cases, astigmatism can be treated when corrective treatment of myopia or hyperopia is performed.

Figure 11:
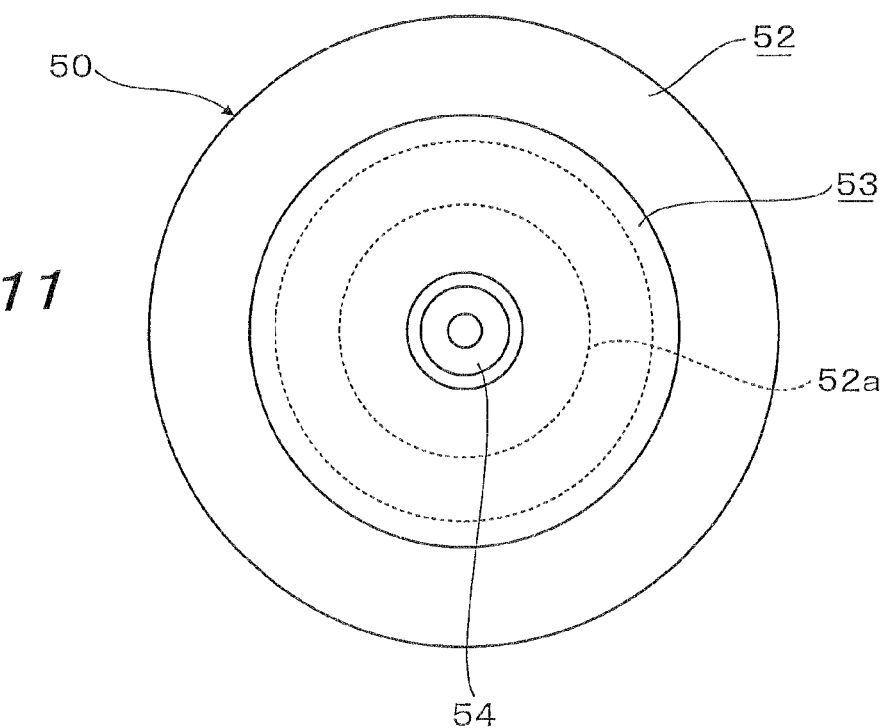
FIG. 11 is a plan view showing another embodiment of a vision corrective jig for hyperopia of the present invention.
Figure 12:
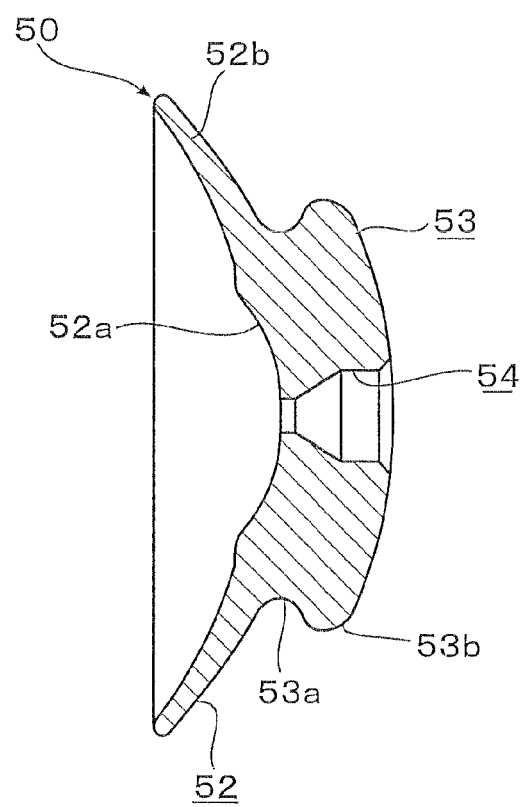
FIG. 12 is a sectional view of the same.

FIGS. 11 and 12 show another embodiment of a vision corrective jig for hyperopia. This vision corrective jig for hyperopia 50 is, in the same way as the vision corrective jig for myopia 1 described above, wholly in a disc shape, and comprises a shape retention part 52 of sucking disc configuration and a grip part 53 in a button shape formed on the outer surface side of the shape retention part 52, and they are made of materials being harmless to human bodies such as glass, metals, and synthetic resins, and integrally molded.

The inner surface of the circumference end surface 52$b$ of the shape retention part 52 is formed in a spherical shape, and a circular, concave portion 52$a$ is formed in the center of inner surface. The concave portion 52$a$ is in a spherical shape curved in the direction of the grip part 53. In addition, a body section 53$a$ of the grip part 53 is narrow in the middle, thereby a flange section 53$b$ is formed. In the central areas of the shape retention part 52 and the grip part 53, a cooling fluid injection hole 54 passing through them is formed. The shape of this cooling fluid injection hole 54 is same as that of the vision corrective jig for myopia 1 described above.

Also, in case of this vision corrective jig for hyperopia 50, various types of vision corrective jigs 50 with such as different curvatures of inner surface of the shape retention part 52, different diameters and curvatures of the concave portion 52$a$, and different diameters of the cooling fluid injection hole 54 are prepared, and the most suitable vision corrective jig 50 is selected depending on the degree of hyperopia.

The vision corrective jig for hyperopia 50 may be used when the cornea suction is not needed. That is, when corneal hardness, degree of hyperopia, corneal shape, and the like are examined, and it is considered that the corneal tissue is soft, hyperopia is mild, and a slight deformation of the cornea is sufficient, firstly the cornea is warmed and softened sufficiently, then the vision corrective jig for hyperopia 50 is attached to the exact position of the eyeball in the same way as that of vision corrective jigs 1 and 10. During the procedure, the vision corrective jig 50 is preferably pushed to the cornea a little harder.

By keeping this situation for the predetermined time, the cornea is corrected to the shape after the inner surface of the shape retention part 52 of the vision corrective jig for hyperopia 50. That is, a slightly hollow section of the central cornea bulges out after the concave portion 52a of the shape retention part 52.

If it is considered that the cornea is reshaped, the warming and softening procedure is discontinued, then the cooling fluid injection tool 20 or 30 shown in FIG. 5 to FIG. 8 is inserted into the cooling fluid injection hole 54, and the central part of the cornea is quenched by spraying the cooling fluid, thereby, the cells in the slightly bulged central part of the cornea contract and the cornea is corrected to the normal shape. When the cornea may resume its previous shape by quenching, by attaching the corneal corrective jig 10 to the eyeball shown in FIG. 4, and using the cooling fluid injection tool 40 shown in the FIG. 9, the peripheral section of the cornea except for the central convex section can be quenched. Since the quenching method is same as described above, and its explanation is omitted.

The embodiments described above are examples of the present invention, and for easier handling, such as shapes, configurations of parts of the vision corrective jigs and the cooling fluid injection tools may be modified.

The invention claimed is:

1. A vision corrective jig is configured to wrap an eyeball to be corrected and reshape a cornea therein softened by warming, comprising:
   a shape retention part of sucking disc configuration including an inner surface side formed for contacting with the cornea of the eyeball to be corrected; and
   a grip part formed on the outer surface side of the shape retention part,
   wherein the inner surface side formed for contacting the cornea of the shape retention part is flattened and a cooling fluid injection hole passing through the shape retention part and the grip part is formed; and
   wherein the cooling fluid injection hole formed in the grip part has a diameter that is larger than a diameter of the cooling fluid injection hole formed in the shape retention part.

2. A vision corrective jig according to claim 1, wherein the cooling fluid injection hole is formed at the central areas of the shape retention part and the grip part, and wherein the diameters formed are large enough for a wearer to see outside through the cooling fluid injection hole.

3. A vision corrective jig according to claim 1, wherein the grip part is integrally formed on an outer surface side of the shape retention part in a button shape.

* * * * *